(12) United States Patent
Dorroh et al.

(10) Patent No.: US 7,481,773 B1
(45) Date of Patent: Jan. 27, 2009

(54) SYSTEM AND METHOD OF MONITORING BODY TEMPERATURE

(75) Inventors: Dana C. Dorroh, Raleigh, NC (US); Thomas Marshall Gordon, III, Raleigh, NC (US); Barry H. Beith, Cary, NC (US)

(73) Assignee: Humancentric Health, LLC, Cary, NC (US)

(*) Notice: Subject to any disclaimer, the term of this patent is extended or adjusted under 35 U.S.C. 154(b) by 0 days.

(21) Appl. No.: 10/961,345

(22) Filed: Oct. 8, 2004

(51) Int. Cl.
*A61B 5/01* (2006.01)
*A61C 5/14* (2006.01)
(52) U.S. Cl. ........................ 600/549; 128/861
(58) Field of Classification Search ............... 600/549; 128/859–862; 119/831, 833; 433/71; 374/100, 374/208
See application file for complete search history.

(56) References Cited

U.S. PATENT DOCUMENTS

| | | | | |
|---|---|---|---|---|
| 5,108,364 A | * | 4/1992 | Takezawa et al. | 604/43 |
| 6,491,037 B1 | * | 12/2002 | Mortenson | 128/859 |
| 6,811,306 B2 | * | 11/2004 | Gerlitz | 374/121 |
| 2003/0040679 A1 | * | 2/2003 | Weber et al. | 600/549 |
| 2003/0154990 A1 | * | 8/2003 | Parker | 128/861 |
| 2004/0076219 A1 | * | 4/2004 | Madison et al. | 374/159 |
| 2004/0181166 A1 | * | 9/2004 | Williford et al. | 600/549 |

FOREIGN PATENT DOCUMENTS

WO   WO 9428384 A1 * 12/1994

* cited by examiner

*Primary Examiner*—Charles A Marmor, II
(74) *Attorney, Agent, or Firm*—Coats & Bennett, P.L.L.C.

(57) ABSTRACT

A body temperature monitoring system comprises a mouth guard, a temperature-sensing unit associated with the mouth guard, and an indicator unit responsive to the temperature-sensing unit. The indicator unit indicates if a body temperature sensed by the temperature-sensing unit is outside of a pre-selected range. The indicator unit may be programmed to actuate an indicator when the temperature-sensing unit senses one or more temperatures that fall outside the pre-selected range. In one implementation, the indicator unit receives a string of multiple temperature readings and determines which temperatures are valid and invalid, and averages the valid temperatures. A method of monitoring a person's body temperature that parallels the above device is also described.

19 Claims, 4 Drawing Sheets

SYSTEM AND METHOD OF MONITORING BODY TEMPERATURE

FIELD OF THE INVENTION

The present invention relates to systems and methods of monitoring body temperature, and more particularly to systems and methods of monitoring body temperature providing mouth guards.

BACKGROUND OF THE INVENTION

In recent years, recognition has become widespread of the problem of excessive changes to core body temperature during physical exertion. The problem has the potential to affect a broad swath of the population, including athletes from the professional level to the recreational. Excessive body temperature may manifest itself in the form of heat stroke or heat exhaustion. In the other extreme, hypothermia may result from excessive reduction of body temperature.

Monitoring body temperature during athletic events poses special challenges. The wearer must maintain mobility, so that devices protruding from the mouth or ears are impractical. Furthermore, it is often normal and safe for body temperature to fluctuate substantially during physical exertion, so that it may be necessary to monitor body temperature over some period of time in order to accurately determine whether body temperature is outside of a safe range. Additionally, the measurement of body temperature should accurately measure core body temperature. For this reason, systems and methods that monitor skin temperature are deficient, because temperature often at the skin may differ significantly from core body temperature.

Thus, there remains a need for a system or method for effectively monitoring body temperature during physical exertion.

SUMMARY OF THE INVENTION

The system of the present invention comprises a mouth guard, a temperature-sensing unit associated with the mouth guard, and an indicator unit responsive to the temperature-sensing unit. The mouth guard may be configured to position the temperature-sensing unit proximate the maxillary arch of the mouth of a wearer. The indicator unit indicates when the body temperature sensed by the temperature-sensing unit is outside of a pre-selected range. The indicator unit may be configured to provide a physical stimulus to the wearer of the mouth guard and/or may comprise a visible or audible indicator. The indicator unit may be associated with the mouth guard or it may comprise a separate assembly. The indicator unit may be configured to process outputs from the temperature sensing unit by determining whether each output is valid and determining an average value of valid outputs.

The method comprises steps of integrating a temperature sensor and a mouth guard, processing output from the temperature sensor to determine the average body temperature of a wearer of the mouth guard, and generating a temperature indication based on the average body temperature. The processing may comprise accepting output at fixed time intervals, discarding invalid output, and/or determining an average body temperature based on valid output. The temperature indication may comprise a visible indication, an audible indication and/or a physical stimulation to the wearer. The temperature indication may indicate that the average body temperature is outside of a pre-selected range. The processing and generating steps may be carried out in an assembly separate from the integrated mouth guard and temperature sensor, and that assembly may communicate with the temperature sensor through a wireless interface.

DETAILED DESCRIPTION OF THE INVENTION

Figure 1:
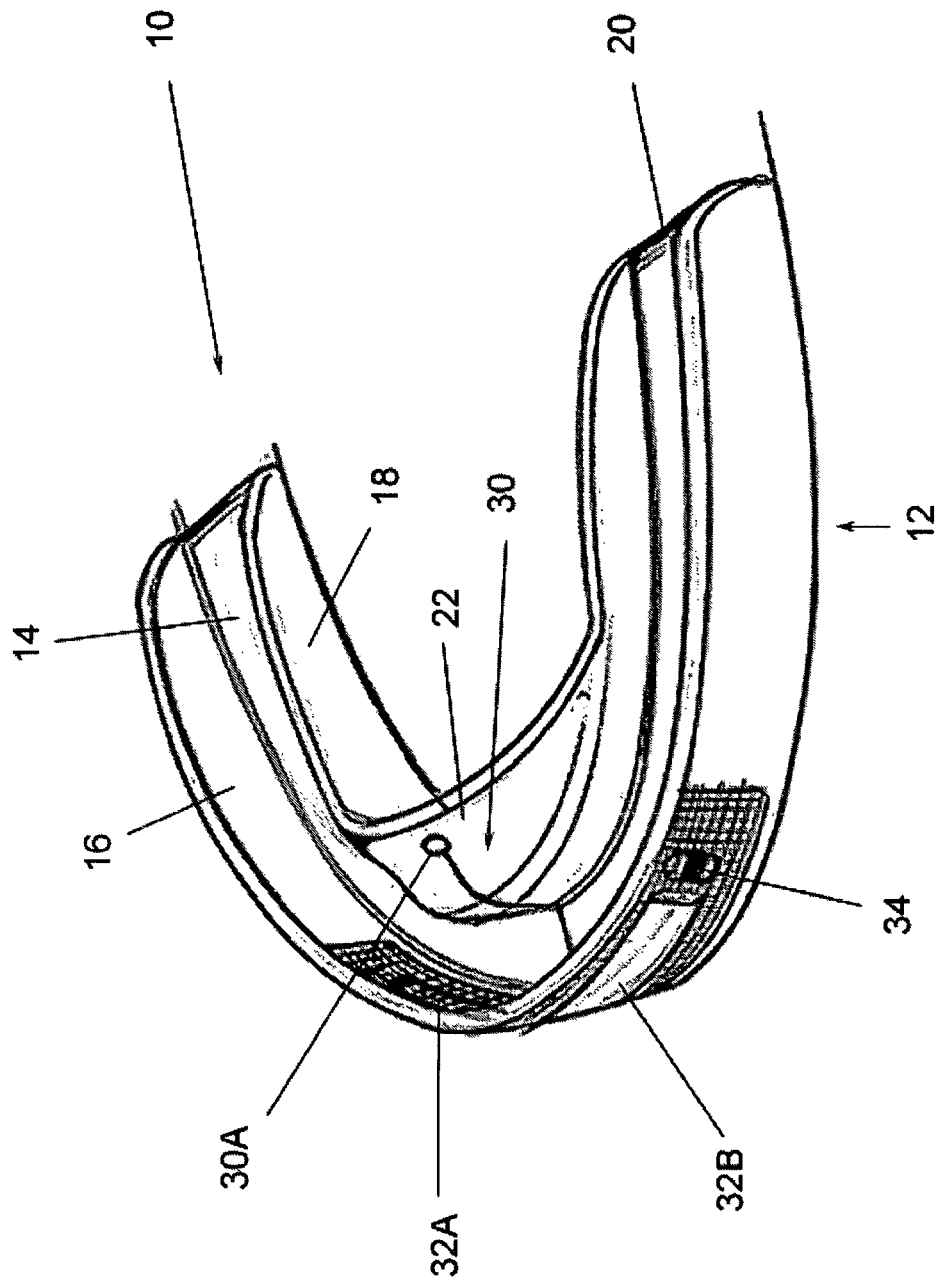
FIG. 1 is a perspective view of the temperature monitoring system of the present invention.

With further reference to the drawings, the temperature monitoring system of the present invention is shown therein and indicated generally by the numeral 10. Temperature monitoring system 10 comprises a mouth guard indicated generally by the numeral 12 and a temperature sensing unit indicated generally by the numeral 30. Temperature sensing unit 30 is integrated or associated with the mouth guard 12. Further, the temperature monitoring system 10 comprises an indicator unit 32. In one embodiment, as discussed below, indicator unit 32 is integrated into the mouth guard 12. However, as will be discussed subsequently herein, one or more components of the indicator unit 32 can be located remotely from the mouth guard 12.

Returning to the mouth guard 12, the same includes a main body that is configured to fit within a wearer's mouth. Mouth guard 12 would preferably be constructed of the same material and in the same manner as conventional mouth guards of the type used by athletes, for example. Structurally, mouth guard 12 includes a curved or non-linear teeth channel 14. In the case of the mouth guard 12 shown in FIG. 1, teeth channel 14 is designed to receive the upper teeth of the wearer. Teeth channel 14 includes a front curved portion 16, a back curved portion 18 and a bottom portion 20. Formed generally centrally about the rear portion of the mouth guard 12 is a maxillary arch 22. The maxillary arch 22 is configured to rest adjacent an upper portion of the roof of the wearer's mouth adjacent the teeth.

Figure 2:
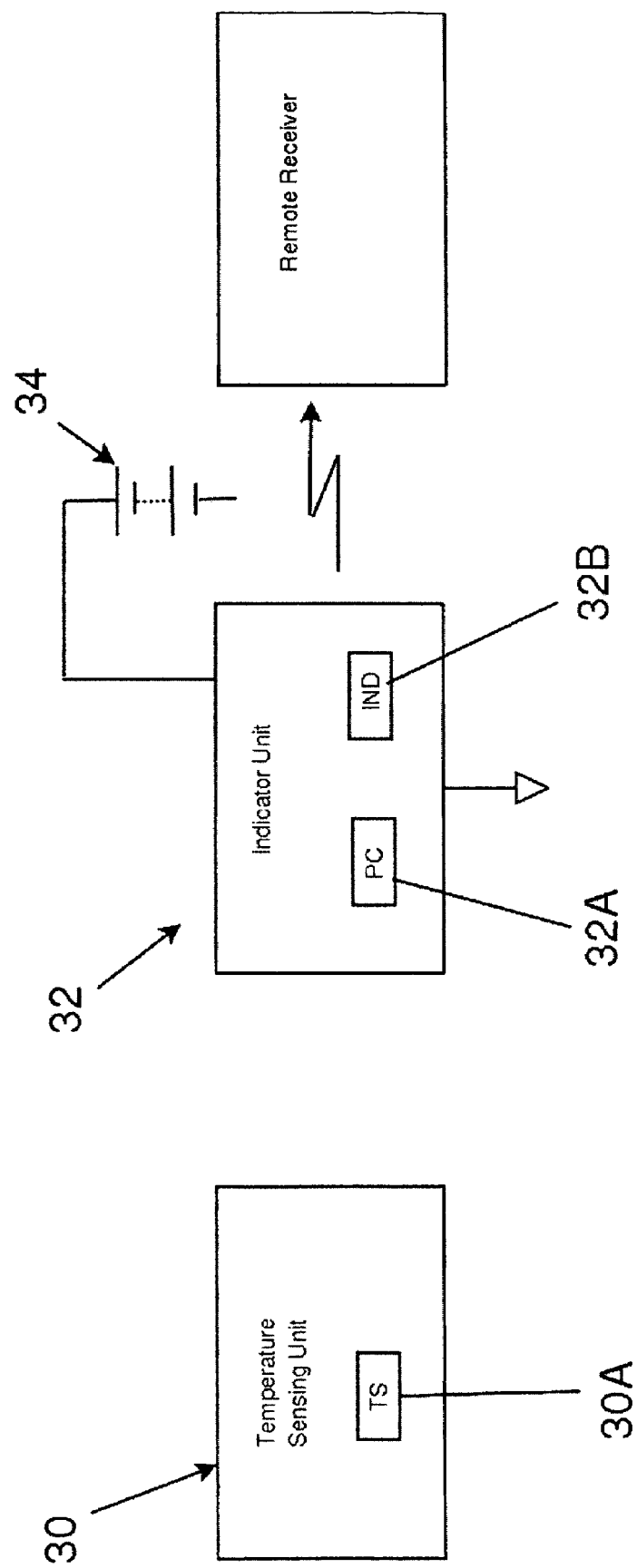
FIG. 2 is a schematic illustration of the temperature sensing unit and the indicator unit that forms a part of the temperature monitoring system of the present invention.

Integrated into the mouth guard 12 is the temperature sensing unit 30. As schematically illustrated in FIG. 2, temperature sensing unit 30 includes a temperature sensor 30A. Temperature sensor 30A is positioned on the upper surface of the maxillary arch 22. When mouth guard 12 is properly fitted in the wearer's mouth, the temperature sensor 30A as well as portions of the maxillary arch 22 will engage or touch a portion of the roof of the wearer's mouth. Various conventional temperature sensors can be provided. In one embodiment it is contemplated that the temperature sensor 30A would be a platinum temperature sensor that would be operative to measure or sense temperature where a current is directed through the platinum temperature sensor. It should be appreciated that the temperature sensor 30A could be incorporated into the mouth guard 12 in other ways. For example, the temperature sensor 30A could be embedded, attached, or fastened to portions of the main body of the mouth guard 12. In the case of a platinum temperature sensor, such a sensor has the advantage of being inert and non-toxic in the environment of a human mouth. Further, a platinum temperature sensor is advantageous in that it is capable in sensing temperatures accurately in the temperature range typically found in human beings.

As noted before, temperature monitoring system 10 includes an indicator unit 32. Indicator unit 32 functions to receive a temperature reading or a series of temperature readings (which could be in the form of signals) from the temperature sensing unit 30, and based on the received temperature reading or readings, determine if the sensed temperature indicates that the core body temperature is in an abnormal range. If the indicator unit 32 determines that the temperature of the individual wearing the mouth guard 12 is in an abnormal or dangerous range, then the indicator unit 32 functions to alert the individual, or some other individuals in the vicinity of where the activity is occurring, that the core body temperature of this individual is abnormal or lying in or around a dangerous range.

Viewing FIG. 2, the indicator unit 32 is shown schematically. As seen in FIG. 2, indicator unit 32 includes a processing circuit 32A and an indicator 32B. Before discussing the processing circuit 32A, it should be noted that the function of the indicator 32B is to indicate that a person wearing the mouth guard 12 is in danger due to their core body temperature being in a dangerous range. This indication can be performed in various ways. First, the indicator 32B may simply include a light emitting diode (LED). Additionally, the indicator 32B may include an audible device. Further, the indicator 32B may include a device that provides a physical stimulus to the wearer of the mouthpiece. For example, in this regard, the mouthpiece could be provided with a portion or a device that would be responsive to a determination that a dangerous temperature condition exists or is approaching to where the device would provide a physical stimulus to the wearer or would provide some physical indication alerting the wearer of the mouth guard 12 that his or her temperature is in a dangerous region or range or is approaching a dangerous region or range. For example, the main body of the mouth guard 12 could be designed to change shape or configuration in response to the sensed temperature being in a danger region. In addition, a pin-like device could be movably mounted within the mouthpiece to provide the physical stimulus required to alert the wearer of the dangerous core temperature condition.

Also, indicator 32B could include an RF transmitter and a remote receiver. That is, once the processing circuit 32A has determined that a dangerous temperature condition exists, an RF transmitter imbedded or closely associated with the mouthpiece 12 could direct an RF signal to a remote receiver, shown in FIG. 2. The remote receiver upon receiving the RF signal would then provide some type of indication that an abnormal or dangerous core temperature condition had been sensed in the wearer of the mouth guard 12.

It is appreciated that the temperature monitoring system 10 would include a battery 34 for powering the processing unit 32A and in the case of some embodiments providing the necessary electrical current to operate the temperature sensor 30A.

Indicator unit 32 could be wholly incorporated into the mouth guard 12 as shown in FIG. 1. In this case, indicator 32B is in the form of an LED and is secured or dispersed about the front portion 16 of the main body of the mouth guard 12. In this position the LED can be viewed when the wearer of the mouthpiece 12 opens his or her mouth. Processing circuit 32A could also be wholly incorporated into the main body of the mouthpiece 12 along with battery 34.

As alluded to before, the indicator 32B could include an RF transmitter and a remote receiver. In such a case the RF transmitter would be embedded or closely associated with the mouth guard 12. The remote receiver could be located remotely from the mouthpiece 12 and could be in the form of a handheld device. The remote receiver could be configured to receive a group of RF signals emitted from a plurality of mouth guards 12. Each RF signal could include a unique identifier such that temperature readings could be associated with particular individuals. In a case involving an RF transmitter and a remote receiver, the processing circuit 32A could still be embedded, secured or closely associated, with the mouth guard 12. Indicator unit 32 could be remotely located from the mouth guard 12. Ordinary networking devices could be utilized to transmit temperature readings or data representing temperature readings from the temperature sensing unit 30 to a remote indicator unit 32.

Processing unit 32A could assume various forms such as a programmable controller or a programmable logic unit. However, in some embodiments the processing circuit 32A may not be programmable but simply configured to perform set functions in a repetitive or routine way. For example, it is contemplated that the processing circuit would be operative to receive a series of outputs or output signals from the temperature sensing unit 30. These outputs or signals from the temperature sensing unit 30 would be indicative of core temperature values measured by the temperature sensing unit 30. Moreover, the processing circuit 32A could be configured to accept this data at selected time intervals over a certain period of time. For example, the processing circuit could be designed and configured to be received from the temperature sensing unit 30 a temperature reading or value every one minute for a period of five minutes. Upon receiving the five temperature readings, the processing unit 32A would add the temperature readings and divide by the number of readings to yield an average temperature. Then the processing unit 32A would compare the average computed temperature to one or more selected ranges or regions of temperatures. For example, abnormal or dangerous temperature regions would be defined and if the computed average temperature falls within a dangerous temperature region, or even a temperature region of concern, then the processing unit 32A would be operative to actuate the indicator 32B. As discussed before, once the indicator 32B has been actuated, an alert is communicated signaling the danger.

It is appreciated that in measuring core temperatures that it is possible to produce data or temperature readings that are not accurate or unreliable. For example, it may be concluded that temperature readings greater than 40° C. or less than 33° C. are invalid temperatures and should not be used in assessing average core temperatures. Thus, processing circuit 32A would be configured to distinguish between valid and invalid temperature readings. Once a valid temperature range is established, processing unit 32A would automatically disregard all invalid temperatures. When a temperature is deemed by the processing unit 32A to be invalid, the processing unit would also possess the intelligence not to count or average that temperature in a group of temperature readings.

In another embodiment of the present invention, the temperature monitoring system 10 could include a device having the temperature-sensing unit 30 incorporated therein where the device would be inserted into an ear of a person. In this case, core body temperatures are sensed by a temperature sensor and communicated to an indicator unit. The same method or process as described above would follow. The temperature sensor would sense temperature at preselected time intervals and these temperature readings (temperature signals) would be directed to the processing unit 32A where the individual readings or signals would be compared or scrutinized by the processing unit to determine if each reading or signal was valid or invalid. The valid temperature readings would again be added and averaged. If the average core body temperature computed by the processing circuit was within a selected danger range, then the indicator would provide an indication of such. Again, the indicator could constitute a visual indicator, an audible indicator, a device that would provide a physical stimulus to the person, and as discussed above, could entail a transmitter sending a signal to a remote receiver.

Figure 3:
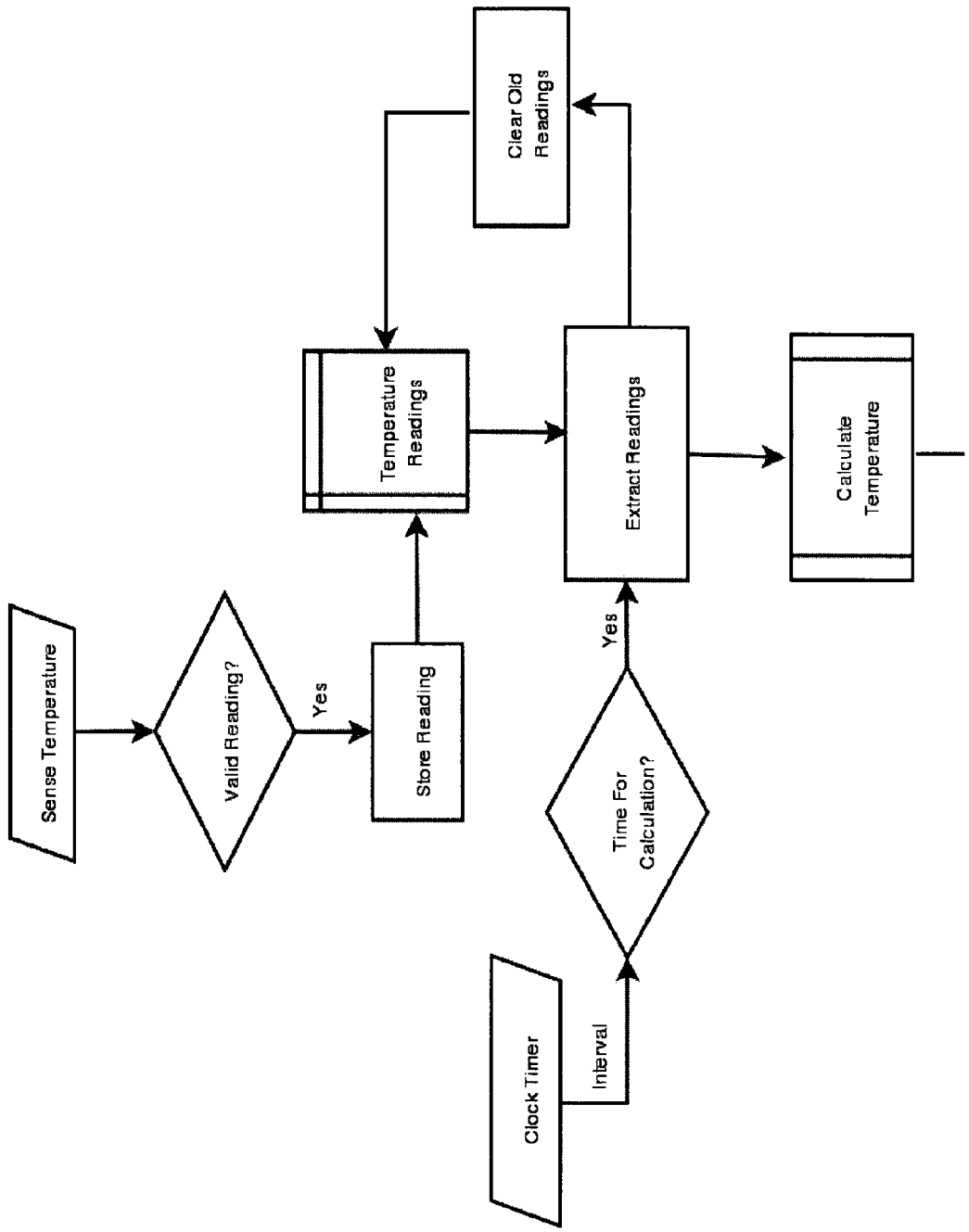
FIG. 3 is a flowchart illustrating functions of the processing circuit that forms a part of the indicator unit.
Figure 4:
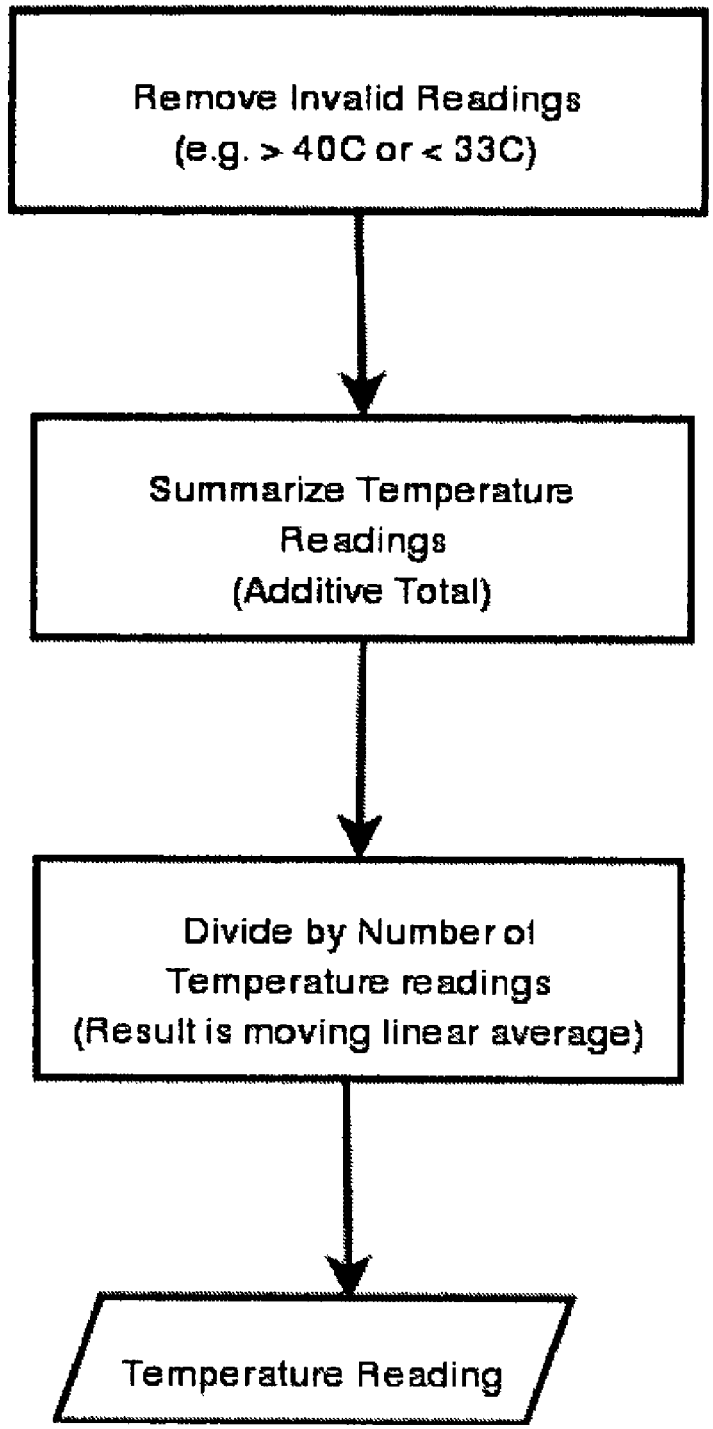
FIG. 4 is a flowchart illustrating the function of the processing circuit in computing an average temperature.

FIGS. 3 and 4 depict an algorithm for sensing and computing core temperatures. These two flowcharts generally summarize the above discussion and particularly the method or approach utilized by the temperature monitoring system 10 in determining if the wearer of the mouth guard 12 has a core temperature that lies in a danger zone.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. A body temperature monitoring system comprising a mouth guard, a temperature-sensing unit associated with the mouth guard, and an indicator unit responsive to the temperature-sensing unit for indicating temperature; wherein the temperature-sensing unit includes a temperature sensor that measures temperature over a selected time interval and generates a series of discrete temperature outputs over the time interval; and the indicator unit includes a processing circuit that receives the series of temperature outputs from the temperature-sensing unit, adds the series of temperature outputs, and calculates an average temperature for the series of temperature outputs, thereby providing a time-averaged temperature for the series of temperature outputs generated over the selected time interval; and wherein the processing circuit disregards temperature readings that lie outside of a selected range.

2. A method of monitoring body temperature comprising steps of:
    integrating a temperature sensor and a mouth guard;
    measuring temperature over a selected time interval with the temperature sensor;
    generating a series of discrete temperature outputs over the time interval with the temperature sensor;
    processing the series of discrete temperature outputs generated by the temperature sensor by calculating an average temperature for the series of discrete temperature outputs and discarding invalid output from the temperature sensor; and
    generating a temperature indication based on the calculated average temperature.

3. The method of claim 2 wherein generating a temperature indication includes actuating an indicator secured to or forming a part of the mouth guard.

4. The method of claim 3 wherein said processing comprises determining average core body temperature based on a plurality of valid outputs from the temperature sensor.

5. The method of claim 2 further including integrating a temperature indicator with the mouth guard such that the temperature indicator is secured to or forms a part of the mouth guard.

6. The method of claim 2 including integrating a battery into the mouth guard.

7. The method of claim 2 further including integrating a processing circuit and a temperature indicator into the mouth guard.

8. The method of claim 2 wherein said processing comprises accepting output from the temperature sensor at fixed time intervals.

9. The method of claim 2 wherein the step of generating a temperature indication comprises generating a visible indication.

10. The method of claim 2 wherein the step of generating a temperature indication comprises physically stimulating a wearer.

11. The method of claim 2 wherein the step of generating a temperature indication comprises indicating that an average core body temperature is outside of a selected range.

12. The method of claim 2 wherein the processing and generating steps are carried out in an assembly separate from the integrated mouth guard and temperature sensor.

13. The method of claim 12 wherein the assembly and the temperature sensor communicate through a wireless interface.

14. A method of monitoring core body temperature comprising the steps of:
    integrating a temperature sensor into a mouth guard that is held within the mouth of a person;
    generating a series of discrete temperature outputs from the temperature sensor over a selected time interval;
    directing the series of discrete temperature outputs from the temperature sensor to a processing circuit;
    adding the temperature outputs with the processing circuit;
    computing a time-averaged temperature for the series of discrete temperature outputs with the processing circuit and wherein the processing circuit only averages temperature outputs that fall within a selected temperature range and disregards temperature outputs that fall outside the selected temperature range; and
    when the computed average temperature is within a selected range, generating a temperature indication.

15. The method of claim 14 wherein generating a temperature indication includes generating a visual or audible signal or providing a physical stimulus to the person.

16. A body temperature monitoring system comprising a mouth guard, a temperature-sensing unit associated with the mouth guard, and an indicator unit responsive to the temperature-sensing unit for indicating temperature; wherein the temperature-sensing unit includes a temperature sensor that measures temperature over a selected time interval and generates a series of discrete temperature outputs over the time interval; and the indicator unit includes a processing circuit that receives the series of temperature outputs from the temperature-sensing unit and only processes temperature outputs that fall within a selected temperature range and disregards temperature outputs that fall outside the selected temperature range.

17. The body temperature monitoring system of claim 16 wherein the processing circuit adds the series of temperature outputs and calculates an average temperature for the series of temperature outputs, thereby providing time averaged temperature for the series of temperature outputs generated over the selected time interval.

18. A method of monitoring body temperature comprising the steps of:
    integrating a temperature sensor and a mouth guard;
    measuring temperature over a selected time interval with the temperature sensor;
    generating a series of discrete temperature outputs over the time interval with the temperature sensor;
    discarding temperature outputs from the temperature sensor that fall outside of a predetermined temperature output range;
    processing temperature outputs from the temperature sensor that fall within the predetermined temperature output range; and
    generating a temperature indication.

19. The method of claim 18 further including calculating a time-averaged temperature for the series of discrete temperature outputs and generating a temperature indication based on the calculated time-averaged temperature.

* * * * *